(12) United States Patent
Di Schiena et al.

(10) Patent No.: US 8,367,636 B2
(45) Date of Patent: Feb. 5, 2013

(54) COMPOSITION BASED ON SALTS OF HYALURONIC ACID FOR TREATING EPITHELIAL LESIONS

(75) Inventors: Michele Giuseppe Di Schiena, Robecco Sul Naviglio (IT); Marco Pinna, Arcisate (IT); Fausto Pinna, Lesmo (IT)

(73) Assignee: Biofarmitalia S.p.A., Milan (IT)

( * ) Notice: Subject to any disclaimer, the term of this patent is extended or adjusted under 35 U.S.C. 154(b) by 686 days.

(21) Appl. No.: 11/839,266

(22) Filed: Aug. 15, 2007

(65) Prior Publication Data

US 2008/0058283 A1   Mar. 6, 2008

(30) Foreign Application Priority Data

Sep. 1, 2006  (IT) .............................. MI2006A1668

(51) Int. Cl.
*A01N 43/04* (2006.01)
*A61K 31/715* (2006.01)

(52) U.S. Cl. ........................................................ 514/54

(58) Field of Classification Search ........................ None
See application file for complete search history.

(56) References Cited

U.S. PATENT DOCUMENTS

| 4,517,295 | A | * | 5/1985 | Bracke et al. | ................. | 435/101 |
| 5,093,487 | A | * | 3/1992 | Brown et al. | ................. | 536/55.1 |
| 5,166,331 | A | * | 11/1992 | della Valle et al. | .......... | 536/55.1 |

FOREIGN PATENT DOCUMENTS

EP    0 444 492 A1    9/1991

OTHER PUBLICATIONS

Viscosity—The Physics Hypertextbook.*
U.S. Appl. No. 13/343,137, filed Jan. 4, 2012, Di Schiena.

* cited by examiner

*Primary Examiner* — Layla Bland
(74) *Attorney, Agent, or Firm* — Oblon, Spivak, McClelland, Maier & Neustadt, L.L.P.

(57) ABSTRACT

Compositions based on physiologically acceptable salts of hyaluronic acid having very low viscosity, usable for the treatment and prevention of epithelial lesions and lesions of the connective tissue.

14 Claims, No Drawings

COMPOSITION BASED ON SALTS OF HYALURONIC ACID FOR TREATING EPITHELIAL LESIONS

BACKGROUND OF THE INVENTION

1. Field of the Invention

The present invention relates to compositions based on physiologically acceptable salts of hyaluronic acid, for the treatment and prevention of lesions of the epithelium and of the connective tissue, both human and animal.

Hyaluronic acid is an acid non-sulphurated mucopolysaccharide, being a basic constituent of the connective tissue. In man and animals, hyaluronic acid is present not only in the connective tissue, but also in important biological fluids such as the vitreous humor, the aqueous humor and in the umbilical cord: it has no toxicity and no contraindications for use on man or on animals.

Hyaluronic acid can be obtained by extraction from natural substances, for example from cocks' crests, or can be produced by biotechnology methods. It has a wide molecular weight spectrum which can reach 15,000,000 depending on the method for its production. Hyaluronic acid is known to be used as the sodium or potassium salt in human therapy and in cosmetics: exogenous application of hyaluronic acid has a beneficial effect favoring connective organization and is also effective in reducing or eliminating inflammatory processes induced by germs producing hyaluronase, it facilitates resolution of phlogistic components, reduces excessive capillary permeability, accelerates tissue repair processes and develops an antiedematogenic action by metabolically binding free water to its molecular structures.

Therapeutic indications of hyaluronic acid comprise dermatopathies originating from escoriative abrasions, ulcers deriving from arteriosclerotic vasculopathies, varicose ulcers, cicatrization delays and surgical operations.

In the cosmetics field, hyaluronic acid is used for its invigorating, tonic, skin repair and hydrating properties.

2. Discussion of the Background

U.S. Pat. No. 4,736,024 describes the use of hyaluronic acid and its salts as a vehicle for pharmacologically active substances in pharmaceutical compositions for topical administration.

EP-B-0444492 illustrates the use of hyaluronic acid (and its salts) of high molecular weight (between 800,000 and 4,000,000) for the treatment and prevention of inflammatory states of the oral mucosa.

EP-B-0138572 describes the therapeutic use of fractions of hyaluronic acid and its salts of average molecular weight between 50,000 and 730,000: the fraction (known as "Hyalastine") of average molecular weight between 50,000 and 100,000 has cicatrizing action on lesions of various kinds; the fraction (known as "Hyalectin") of average molecular weight between 500,000 and 730,000 is used to treat degenerative and traumatic disturbances of the joints of articulations and to improve their functionality. U.S. Pat. No. 4,517,295 describes a fermentation method for preparing hyaluronic acid and/or its salts (in particular sodium hyaluronate) of high purity, very low viscosity and low molecular weight (including less than 10,000, as stated for example in lines 64-68 of column 4 and lines 6-7 of column 5): this patent specifies that the products obtained in this manner can be used as wetting agents, lubricants, in post-operative use (lines 65-68 of column 1) and for eye pathologies (lines 8-13 of column 5).

U.S. Pat. No. 5,093,487 teaches a method for preparing hyaluronic acid and/or its salts in very pure form, having high molecular weight (up to at least 1,800,000: see lines 47-50 of column 2) and low viscosity (see Example 1 and claims 3 and 14). No specific therapeutic or cosmetic use is indicated.

SUMMARY OF THE INVENTION

According to the present invention it has been surprisingly found that if physiologically acceptable salts of hyaluronic acid (in particular in the form of the sodium salt or potassium salt) of viscosity equal to 0 (zero) mPa·s at a concentration of 1% w/v in water at 20° C. and less than 10 mPa·s at a concentration of 6% w/v in water at 20° C. is used to prepare compositions for therapeutic use, both topical, injectable and oral, these compositions exhibit an important cicatrizing activity for lesions of the epithelium and connective tissue of the human and animal body.

The aforestated compositions can be in liquid, semisolid or solid form. The low viscosity enables compositions with particularly high hyaluronic acid concentrations to be obtained, such as those claimed in the present invention and provides various advantages, including in its practical use; in particular, in therapeutic use it enables, for example, a higher quantity of active principle to be administered to increase the therapeutic effect, to achieve greater flexibility in posology which can for example be suitably modulated, and to obtain improved acceptance of treatment by the patient and consequently therapeutic success.

The absence of viscosity or a very low viscosity for a wide range of aqueous sodium hyaluronate concentrations is a particularly important characteristic in preparing compositions in which viscosizing, gelling, thickening etc. ingredients are present, as their rheological characteristics are not modified; compositions of high sodium hyaluronate concentration can also be obtained, for example greater than 20%, including in the presence of water, with rheological characteristics suitable for the intended use.

The compositions of the present invention contain between 0.001% and 100% of at least one physiologically acceptable salt (preferably sodium or potassium salts) of hyaluronic acid having a viscosity of 0 (zero) mPa·s at a concentration of 1% w/v in water at 20° C. and less than 10 mPa·s at a concentration of 6% w/v in water at 20° C.

These compositions can comprise physiologically acceptable excipients compatible with hyaluronic acid and with the intended use.

Preferred excipients are chosen from the group consisting of water, alcohol, natural or synthetic oils, gelling, suspending, emulsifying or thickening products, inert powders, natural and synthetic polymers, sweeteners, aromas, perfumes, colorants, preservatives, and compounds favoring epithelial and connectival absorption.

The present invention also relates to the use of physiologically acceptable salts (such as sodium or potassium salts) of hyaluronic acid having a viscosity of 0 (zero) mPa·s at a concentration of 1% w/v in water at 20° C. and less than 10 mPa·s at a concentration of 6% w/v in water at 20° C. for the preparation of pharmaceutical compositions for treating lesions of the epithelium and of the connective tissue.

Finally, the invention relates also to the method for treating lesions of the epithelium and of the connective tissue by administering to the patients a composition as indicated hereabove.

DETAILED DESCRIPTION OF THE INVENTION

Some non-limiting examples are described hereinafter to clarify the understanding of the present invention.

Example 1

In accordance with the procedure described in Example 1 of U.S. Pat. No. 5,093,487, the sodium salt of hyaluronic acid is prepared having an average molecular weight of 1,800,000 and a viscosity of 9 mPa·s at a concentration of 1% w/v in water at 20° C.

This salt can be used at a concentration of 0.005% to prepare a composition for treating lesions of the vaginal and oral epithelium.

Example 2

Again in accordance with the teachings of Example 1 of U.S. Pat. No. 5,093,487, the sodium salt of hyaluronic acid is prepared having an average molecular weight of 1,000,000 and a viscosity of 5 mPa·s at a concentration of 1% w/v in water at 20° C.

The salt obtained can be used to prepare a composition (in which the hyaluronic acid sodium salt has a concentration of 5%) which can be solid, or in the form of tablets to be swallowed, or of the type commonly known as chewing gum.

This composition can be used to treat lesions of the oral, pharyngeal and esophageal cavity.

Example 3

Using the method described in U.S. Pat. No. 4,517,295, hyaluronic acid as sodium hyaluronate is prepared having an average molecular weight of 10,000 and a viscosity of 1.5 mPa·s at a concentration of 6% w/v in water at 20° C. The compound obtained is used to prepare an injectable liquid composition (in which the compound is present in a concentration of 10%), in particular for treating internal traumatic and surgical lesions and for treating ocular lesions and lesions of the auditory duct. A compound of the aforedescribed type is marketed by the French company SOLIANCE with the symbol HA TBPM.

Example 4

Again in accordance with the teachings of U.S. Pat. No. 4,517,295, hyaluronic acid as sodium hyaluronate is prepared having an average molecular weight of 27,000 and a viscosity of 0.5 mPa·s at a concentration of 2% w/v in water at 20° C.

This product can be used to prepare powders (consisting of 100% of the product) usable in odontostomatology, for example after dental extractions.

A product with the aforestated characteristics is produced by the French company SOLIANCE with the name Renovhyal.

Example 5

Using the same method as Examples 3 and 4, hyaluronic acid as sodium hyaluronate is prepared having an average molecular weight of 50,000 and a viscosity of 4 mPa·s at a concentration of 5% w/v in water at 20° C. This product can be used to prepare a cream or gel (in which the product is present in a concentration of 1%) for treating lesions of the cutis or of the mucosa (anal, vaginal).

This product is also available from the French company SOLIANCE, again with the brand name Renovhyal.

The invention claimed is:

1. A composition for treating lesions of the epithelium and of the connective tissue, comprising between 0.001% and 100% of at least one physiologically acceptable salt of hyaluronic acid, and wherein the physiologically acceptable salt of hyaluronic acid has the following property:
   a viscosity of 0 (zero) mPa·s at a concentration of 1% w/v in water at 20° C., and less than 10 mPa·s at a concentration of 6% w/v in water at 20° C.

2. The composition according to claim 1, wherein said physiologically acceptable salts of are selected from the group consisting of sodium and potassium salts of hyaluronic acid.

3. The composition as claimed in claim 1, additionally comprising excipients compatible with hyaluronic acid and with their use in treating the indicated lesions.

4. A method for treating lesions of the epithelium and of the connective tissue which comprises administering to a patient suffering from said lesions a composition according to claim 1.

5. The composition as claimed in claim 2, additionally comprising excipients compatible with hyaluronic acid and with their use in treating the indicated lesions.

6. The composition as claimed in claim 1, which is in liquid form.

7. The composition as claimed in claim 1, which is in semisolid form.

8. The composition as claimed in claim 1, which is in solid form.

9. A method for treating lesions of the epithelium and of the connective tissue which comprises administering to a patient suffering from said lesions a composition according to claim 2.

10. A method for treating lesions of the epithelium and of the connective tissue which comprises administering to a patient suffering from said lesions a composition according to claim 3.

11. A method for treating lesions of the epithelium and of the connective tissue which comprises administering to a patient suffering from said lesions a composition according to claim 5.

12. A method for treating lesions of the epithelium and of the connective tissue which comprises administering to a patient suffering from said lesions a composition according to claim 6.

13. A method for treating lesions of the epithelium and of the connective tissue which comprises administering to a patient suffering from said lesions a composition according to claim 7.

14. A method for treating lesions of the epithelium and of the connective tissue which comprises administering to a patient suffering from said lesions a composition according to claim 8.

* * * * *